United States Patent
Chen

(10) Patent No.: US 10,330,633 B2
(45) Date of Patent: *Jun. 25, 2019

(54) SYSTEM FOR COMMUNICATING INFORMATION FROM AN ARRAY OF SENSORS

(71) Applicant: Genia Technologies, Inc., Santa Clara, CA (US)

(72) Inventor: Roger J. A. Chen, Saratoga, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 228 days.

This patent is subject to a terminal disclaimer.

(21) Appl. No.: 15/380,721

(22) Filed: Dec. 15, 2016

(65) Prior Publication Data

US 2017/0199151 A1 Jul. 13, 2017

Related U.S. Application Data

(63) Continuation of application No. 13/272,109, filed on Oct. 12, 2011, now Pat. No. 9,581,563.

(Continued)

(51) Int. Cl.
*G01N 27/327* (2006.01)
*G01N 33/487* (2006.01)
(Continued)

(52) U.S. Cl.
CPC ....... *G01N 27/3278* (2013.01); *C12Q 1/6874* (2013.01); *G01N 27/44791* (2013.01); *G01N 33/48721* (2013.01)

(58) Field of Classification Search
CPC ............ Y10T 307/826; Y10T 307/858; Y10T 307/865; G01N 27/3278; G01N 33/48721
See application file for complete search history.

(56) References Cited

U.S. PATENT DOCUMENTS 5,235,267 A 8/1993 Schoneberg
5,541,851 A 7/1996 Sato
(Continued)

FOREIGN PATENT DOCUMENTS

CN 103193189 7/2013
EP 1712891 10/2006
(Continued)

OTHER PUBLICATIONS

Chen et al., Probing Single DNA Molecule Transport using Fabricated Nanopores, (Nano Lett, 2004, 4(11), pp. 2293-2298).
(Continued)

*Primary Examiner* — Fritz M Fleming
(74) *Attorney, Agent, or Firm* — Genia Technologies, Inc,

(57) ABSTRACT

A system for communicating information from an array of sensors is disclosed. The system comprises a sensor array that includes a plurality of sensors, wherein each sensor senses a physical property of a material that is in communication with the sensor. The system further comprises signal processing circuitry associated with each sensor that integrates the output of the sensor over time and compares the integrated output to a threshold. The system further comprises a communication network coupled to the signal processing circuitry that outputs information indicating that the integrated output corresponding to a given sensor has reached the threshold.

14 Claims, 6 Drawing Sheets

Related U.S. Application Data

(60) Provisional application No. 61/435,700, filed on Jan. 24, 2011.

(51) Int. Cl.
*C12Q 1/6874* (2018.01)
*G01N 27/447* (2006.01)

(56) References Cited

U.S. PATENT DOCUMENTS

| | | | |
|---|---|---|---|
| 5,747,805 | A | 5/1998 | Youngquist |
| 7,468,271 | B2 | 12/2008 | Golovchenko et al. |
| 7,572,624 | B2 | 8/2009 | Gumbrecht |
| 9,581,563 | B2 * | 2/2017 | Chen ............... G01N 33/48721 |
| 9,605,307 | B2 | 3/2017 | Chen |
| 9,869,655 | B2 * | 1/2018 | Chen ............... G01N 33/48721 |
| 2003/0102263 | A1 | 6/2003 | Lopez |
| 2004/0053337 | A1 | 3/2004 | Yamazaki |
| 2004/0262636 | A1 | 12/2004 | Yang |
| 2005/0239134 | A1 | 10/2005 | Gorenstein |
| 2006/0105373 | A1 | 5/2006 | Pourmand |
| 2006/0246497 | A1 | 11/2006 | Huang |
| 2008/0094076 | A1 | 4/2008 | Hibbs |
| 2010/0078325 | A1 | 4/2010 | Oliver |
| 2011/0168551 | A1 | 7/2011 | White |
| 2015/0060276 | A1 | 3/2015 | Golovchenko |

FOREIGN PATENT DOCUMENTS

| | | |
|---|---|---|
| JP | 2004333485 | 11/2004 |
| JP | 2005538377 | 12/2005 |
| JP | 2008207703 | 3/2008 |
| JP | 2010502936 | 1/2010 |
| WO | WO-03095617 | 11/2003 |
| WO | WO-2007115694 | 10/2007 |
| WO | WO-2008079169 | 7/2008 |
| WO | WO-2009005547 | 1/2009 |
| WO | WO-2009047703 | 4/2009 |
| WO | WO-2009077734 | 6/2009 |
| WO | WO-2009138760 | 11/2009 |
| WO | WO-2010044932 | 4/2010 |
| WO | WO-2013011879 | 1/2013 |

OTHER PUBLICATIONS

Schuster et al,, Sell-Assembled α-Hemolysin Pores in an S-Layer-Supported Lipid Bilayer, Biochimica et Biophysica Acta 1370, (1998) 280-288.

Thei et al., Parallel Recording of Single Ion Channels: A Heterogeneous System Approach, IEEE Transactions on Nanotechnology, vol. 9, No, 3, May 2010.

Axopatch 2008 Patch Clamp Theory and Operation, Mar. 1999 (Year: 1999).

Jiang et al. "Fabrication of sponge-like nanoporous platinum electrocatalysts for oxygen reduction through alloying and dealloying processes." Journal of University of Science and Technology of China. Jun. 30, 2008. vol. 38 No. 5. pp. 614-622.

Kumar, et al. PEG-labeled nucleotides and nanopore detection for single molecule DNA sequencing by synthesis. Sci Rep. 2012;2:684. Epub Sep. 21, 2012.

Wang et al., An Intergrated, Low Noise Patch-Clamp Amplifier for Biological Nanopore Applications, 32nd Annual International Conference of IEEE EMBS, Buenos Aires, Argentina Aug. 31-Sep. 4, 2010.

* cited by examiner

SYSTEM FOR COMMUNICATING INFORMATION FROM AN ARRAY OF SENSORS

CROSS REFERENCE TO OTHER APPLICATIONS

This application is a continuation of U.S. patent application Ser. No. 13/272,109, entitled SYSTEM FOR COMMUNICATING INFORMATION FROM AN ARRAY OF SENSORS, filed Oct. 12, 2011, which claims priority to U.S. Provisional Patent Application No. 61/435,700, entitled SYSTEM FOR COMMUNICATING INFORMATION FROM AN ARRAY OF SENSORS, filed Jan. 24, 2011, both of which are incorporated herein by reference for all purposes.

BACKGROUND OF THE INVENTION

Advances in micro-miniaturization within the semiconductor industry in recent years have enabled biotechnologists to begin packing their traditionally bulky sensing tools into smaller and smaller form factors, onto so-called biochips. It would be desirable to develop techniques for biochips.

BRIEF DESCRIPTION OF THE DRAWINGS

Various embodiments of the invention are disclosed in the following detailed description and the accompanying drawings.

DETAILED DESCRIPTION

Figure 1:
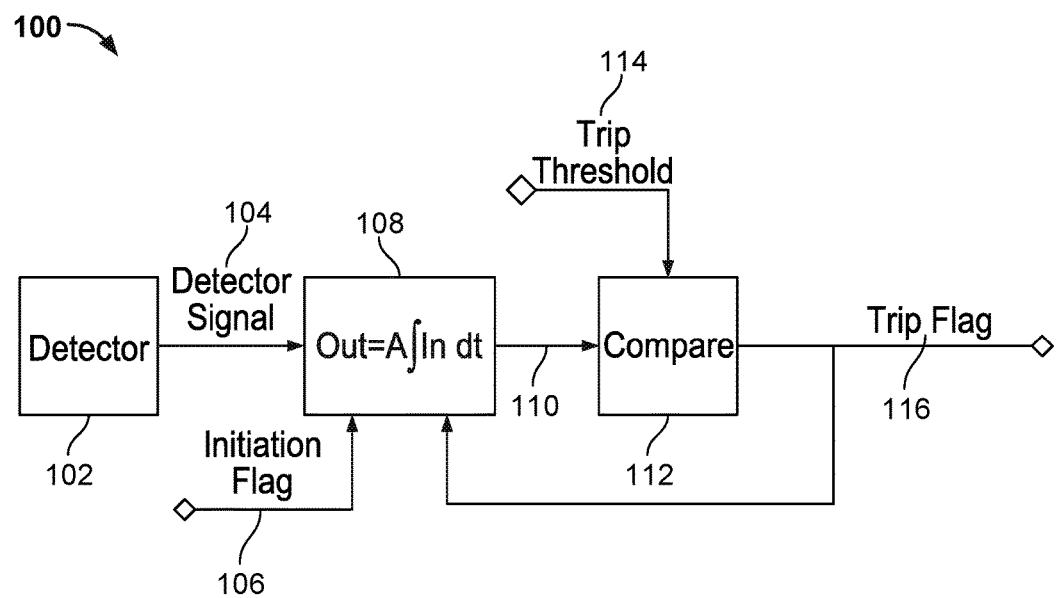
FIG. 1 is a block diagram illustrating an embodiment of a sensor circuit 100 for measuring a physical property within a single cell in a biochip.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

In various embodiments, the techniques described herein are implemented in a variety of systems or forms. In some embodiments, the techniques are implemented in hardware as an application-specific integrated circuit (ASIC) or a field-programmable gate array (FPGA). In some embodiments, a processor (e.g., an embedded one such as an ARM core) is used where the processor is provided or loaded with instructions to perform the techniques described herein. In some embodiments, the technique is implemented as a computer program product which is embodied in a computer readable storage medium and comprises computer instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Advances in micro-miniaturization within the semiconductor industry in recent years have enabled biotechnologists to begin packing their traditionally bulky sensing tools into smaller and smaller form factors, onto so-called biochips. These chips are essentially miniaturized laboratories that can perform hundreds or thousands of simultaneous biochemical reactions. Biochips enable researchers to quickly screen large numbers of biological analytes for a variety of purposes, from disease diagnosis to detection of bioterrorism agents.

Typically, a biochip includes a large array of cells. For example, a biochip for nucleotide sequencing may contain thousands or millions of single cells in an array. Each cell includes a molecular complex composed of monomers that make up an oligomeric nanopore and a single strand of DNA, and anything bound to that single strand of DNA. The nanopore is a small hole in an electrically insulating membrane that can be used as a single-molecule detector. A nanopore may be formed using a biological material, such as a-hemolysin or MspA. A nanopore may be formed using a solid-state material, such as a semiconductor material. When a small voltage is applied across a molecular complex containing a nanopore, an ionic current through the molecular complex can be measured to provide information about the structure of a molecule transiting the molecular complex. In a single cell of the array, an electrical circuit may be used for controlling the electrical stimulus applied across a lipid bilayer which contains a nanopore, and for detecting the electrical patterns, or signatures, of a molecule passing through the nanopore. In order to reduce the cost of the array, physically small single cells with highly sensitive sensors therein are desirable.

FIG. 1 is a block diagram illustrating an embodiment of a sensor circuit 100 for measuring a physical property within a single cell in a biochip. As shown in FIG. 1, a physical property, e.g., a current, voltage, or charge, is detected by detector 102 as detected signal 104. Sensor circuit 100 may be used to measure the mean value of detected signal 104 without sampling as described further below.

In some embodiments, an initiation flag 106 resets an integrating amplifier 108 and starts a continuous integration of detected signal 104 over time. Integrated output 110 is compared with a trip threshold 114 using a comparator 112. When integrated output 110 reaches trip threshold 114, a trip flag 116 may be used as a feedback signal to integrating amplifier 108 for terminating the integration of detected signal 104. For example, when trip flag 116 is "on" or asserted, the integration is terminated. The duration of time between the assertion of initiation flag 106 and the assertion of trip flag 116 is proportional to the mean value of detected signal 104, e.g., the mean value of a current. Accordingly, the "on" and "off" of trip flag 116 (only 1 bit of information) may be sent from the cell to an external processor for calculating the mean value of detected signal 104. Alternatively, the "on/off" information may be sent from the cell to an external storage for delayed processing. For example, the clock cycles at which initiation flag 106 and trip flag 116 are respectively asserted may be recorded in an external storage. The number of clock cycles between the two asserted flags may then be used to determine the mean value of detected signal 104 at a later time.

In some embodiments, more accurate results may be obtained by integrating detected signal 104 over multiple integrating cycles. For example, the determined mean value of detected signal 104 may be further averaged over multiple integrating cycles. In some embodiments, initiation flag 106 is based at least in part on trip flag 116. For example, initiation flag 106 may be re-asserted in response to trip flag 116 being asserted. In this example, trip flag 116 is used as a feedback signal for reinitializing integrating amplifier 108, such that another cycle of integration of detected signal 104 may begin as soon as the previous cycle of integration is terminated. Re-asserting initiation flag 106 immediately after trip flag 116 is asserted reduces the portion of time when detector 102 generates a signal that is not integrated and thus not measured. The integration occurs over approximately the entire time that the signal is available. As a result, most of the information of the signal is captured, thereby minimizing the time to obtain an average value for the measured signal.

Shot noise may corrupt trip flag 116 during certain integrating cycles. Accordingly, some embodiments may include logic to determine whether trip flag 116 has been corrupted by shot noise in a particular integrating cycle before trip flag 116 is saved or used for any calculation.

Figure 2:
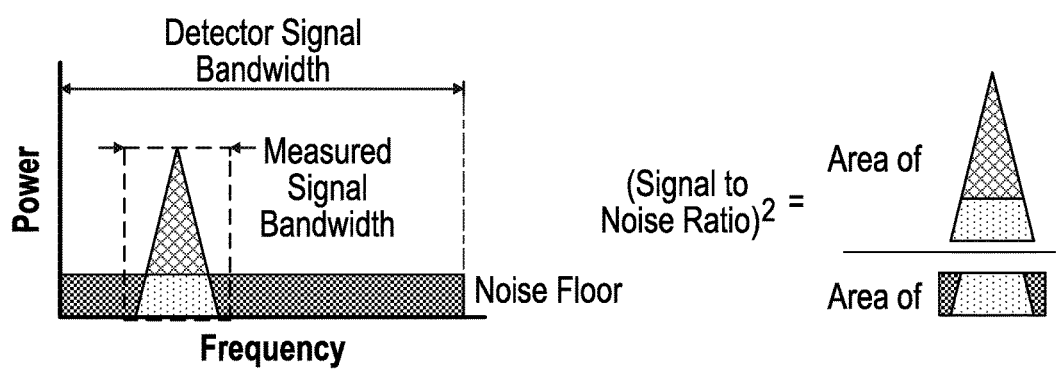
FIG. 2 illustrates that with a constant noise floor, as the measured signal bandwidth decreases, the signal to noise ratio increases, thereby improving the sensitivity of sensor circuit 100 of FIG. 1.

The sensitivity of sensor circuit 100 is maximized by continuously integrating detected signal 102 without sampling. This serves to limit the bandwidth of the measured signal. With continuous reference to FIG. 1, trip threshold 114 and an integration coefficient A set the bandwidth of the measured signal. As integration coefficient A decreases or as trip threshold 114 increases, the measured signal bandwidth decreases. FIG. 2 illustrates that with a constant noise floor, as the measured signal bandwidth decreases, the signal to noise ratio increases, improving the sensitivity of sensor circuit 100. In some embodiments, the measured signal bandwidth can be dynamically adjusted by varying the trip threshold 114.

Figure 3:
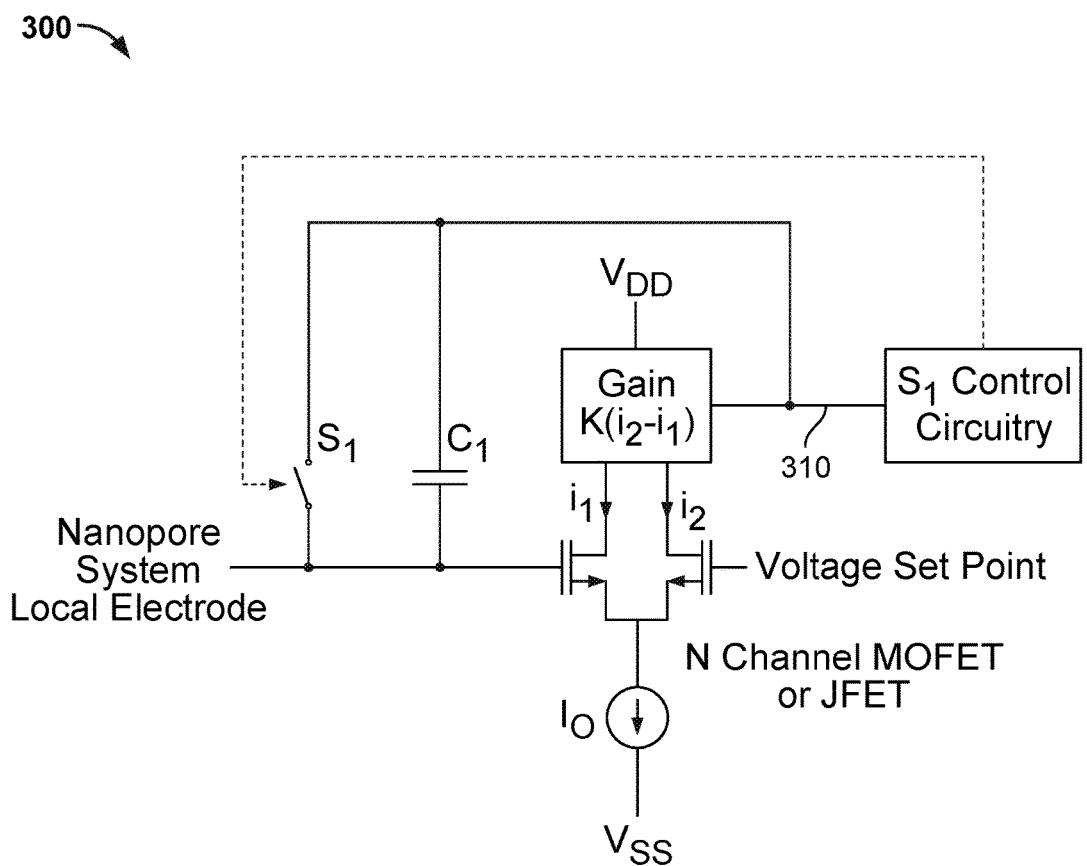
FIG. 3 is a circuit diagram illustrating an embodiment of a sensor circuit 300 for measuring a physical property, e.g., a current, within a single cell in a nanopore array.
Figure 4:
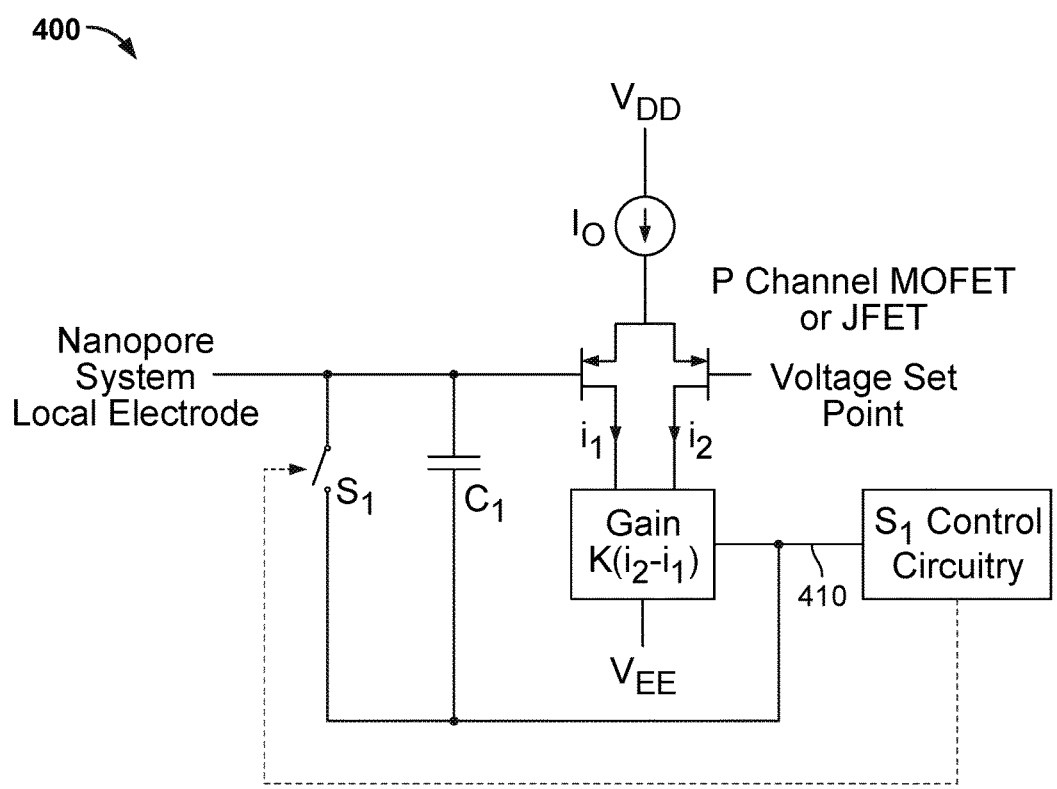
FIG. 4 is a circuit diagram illustrating a second embodiment of a sensor circuit 400 for measuring a physical property within a single cell in a nanopore array.

FIG. 3 is a circuit diagram illustrating an embodiment of a sensor circuit 300 for measuring a physical property, e.g., a voltage, within a single cell in a nanopore array. FIG. 4 is a circuit diagram illustrating a second embodiment of a sensor circuit 400 for measuring a physical property within a single cell in a nanopore array.

With reference to FIGS. 3 and 4, the Si control circuitry includes a comparator and other logic, e.g., logic for switching. The other components of circuit 300 (or circuit 400), including the differential pair, implement an integrating amplifier similar to that in FIG. 1. The input of circuit 300 (or circuit 400) is connected to a nanopore system local electrode.

Figure 5:
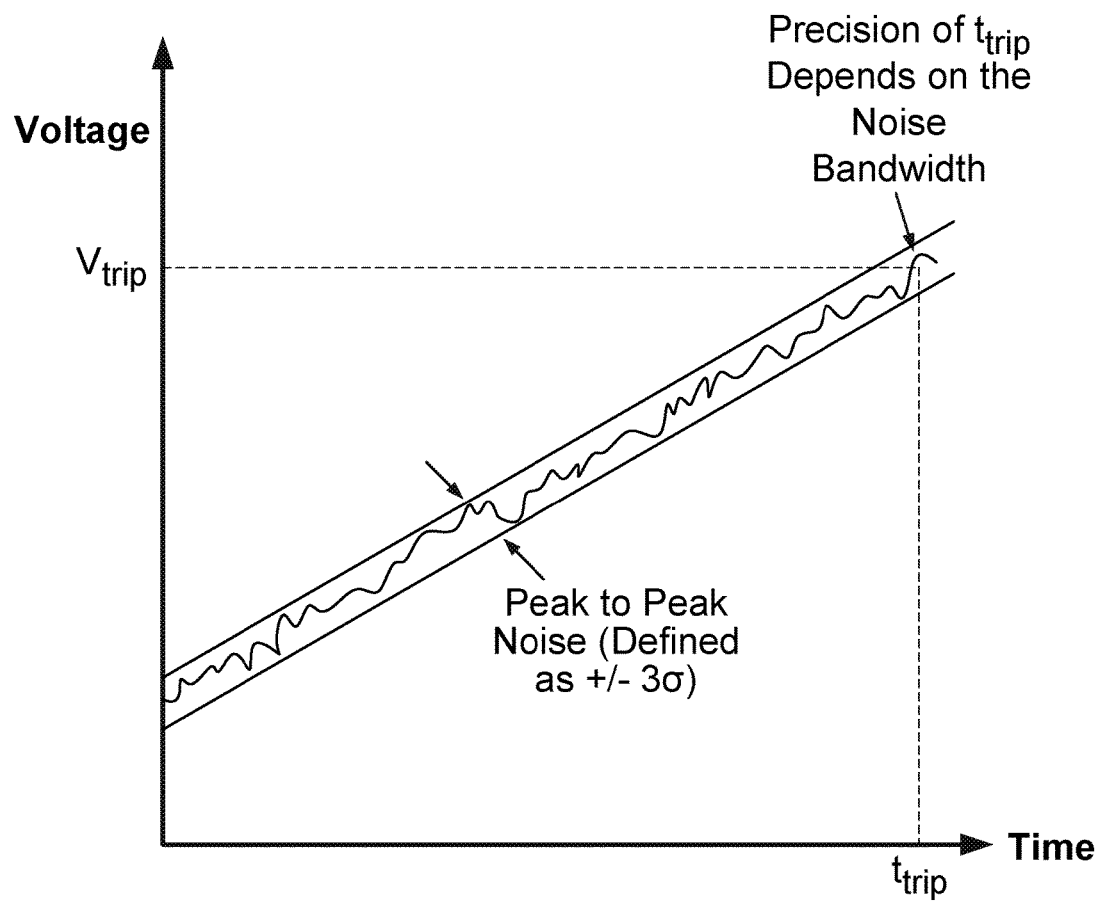
FIG. 5 is a diagram illustrating a plot of the voltage at the output of the integrating amplifier in circuit 300 or circuit 400 versus time.

FIG. 5 is a diagram illustrating a plot of the voltage at 310 (or 410) in circuit 300 (or circuit 400) versus time. In FIG. 5, $t_{trip}$ indicates the mean current flowing through a nanopore. Reducing the noise bandwidth reduces the noise associated with $t_{trip}$. Accordingly, the mean current measurement will have a higher signal to noise ratio (SNR) and be more precise.

The integrating amplifier is configured to amplify only the in-band signal, but not the out-of-band signal. Amplifying all signals amplifies mostly noise since the useful signal's bandwidth is much smaller than the detected signal, resulting in poor SNR. The noise bandwidth may be limited by selecting appropriate values for $C_1$ and $I_O$ in circuits 300 and 400. In some embodiments, $C_1$ and $I_O$ are selected to limit the noise bandwidth between 0.3 Hz and 300 Hz. In some embodiments, the noise bandwidth can be dynamically adjusted by varying the values of $C_1$.

In some embodiments, trip flag 116 for each of the cells are further synchronized with a global clock shared by all the cells within the biochip. For example, trip flag 116 that is synchronized with a global clock may be generated by a pulse generation circuit. After synchronization, trip flag 116 is a single pulse that is in phase with the global clock.

Figure 6:
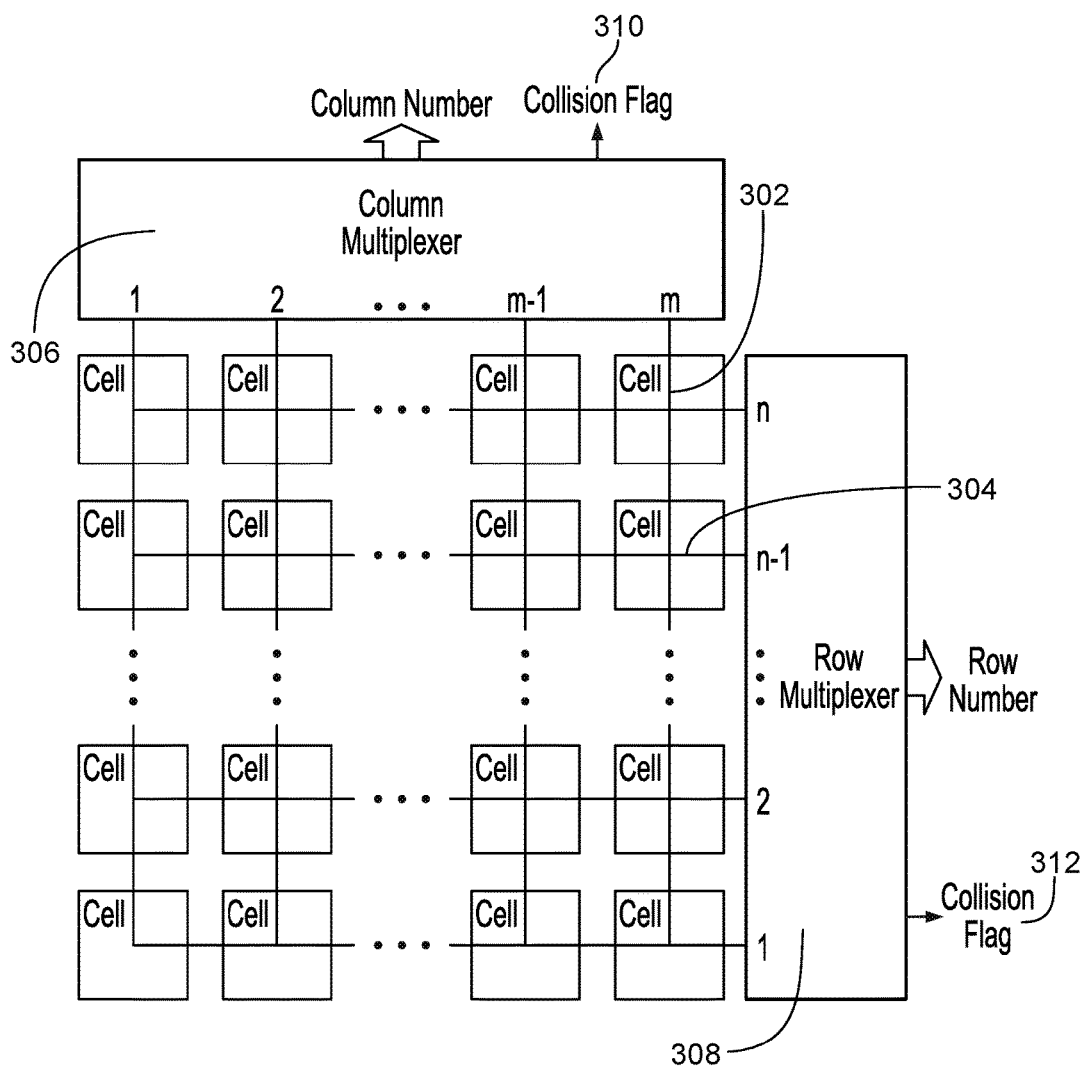
FIG. 6 is a block diagram illustrating an embodiment of a cell array in a biochip.

FIG. 6 is a block diagram illustrating an embodiment of a cell array in a biochip. Each of the cells may contain a sensor circuit 100 for measuring a physical property within the cell as described above. As shown in FIG. 6, the cell array has m columns by n rows of single cells. All the cells in a given column share the same column line 302, and all the cells in a given row share the same row line 304. When trip flag 116 for a particular cell is asserted, the cell asserts its particular column line 302 and row line 304. In order to reduce the pin count of the biochip, a column multiplexer 306 may be used to output a column number ($0-2^m-1$) to indicate which column line 302 has been asserted. Similarly, a row multiplexer 308 may be used to output a row number ($0-2^n-1$) to indicate which row line 304 has been asserted. For example, if trip flag 116 of the cell in the second column and the second row is asserted, the output column and row number is (1, 1). As long as only one cell asserts its trip flag 116 at a time, the reported column and row numbers are sufficient to uniquely identify which particular cell is asserted at a particular time.

The above techniques have a number of advantages over other approaches. The integrating amplifier requires minimal die area and allows for each array site to have its own dedicated measurement circuit. This feature removes the necessity of routing sensitive analog signals to the array periphery and avoids the need for multiplexing, thereby reducing noise. The integrating amplifier requires no pre-amplifier, sample and hold, or anti-aliasing filter, further reducing die area and potential error sources. Since only a single flag is required to denote the completion of a measurement, the integrating approach is an efficient way to communicate data from each array site. Measurements are being made continuously (other than the brief time required to reset the integration capacitor) so data is being gathered almost 100% of the time. Furthermore, each cell and its associated measurement circuit operate autonomously, allowing each cell to track the state of the molecule being measured. As described above, the integrating approach also has inherent signal averaging and noise advantages.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A circuitry for measuring a detected signal from a nanopore, comprising:
   an integrating amplifier integrating a detected signal from a nanopore;
   an initiating flag for resetting the integrating amplifier and starting an integration of the detected signal from the nanopore; and
   a trip flag for terminating the integration of the detected signal from the nanopore, wherein the initiation flag is re-asserted in response to the trip flag being asserted such that the detected signal from the nanopore is integrated over a plurality of integrating cycles.

2. The circuitry of claim 1, wherein the trip flag is asserted in response to an integrated output of the integrating amplifier reaching a predetermined level.

3. The circuitry of claim 2, wherein the trip flag is used as a feedback signal to the integrating amplifier for terminating the integration of the detected signal from the nanopore.

4. The circuitry of claim 1, wherein a state of the trip flag is output to an external processor for processing.

5. The circuitry of claim 1, wherein a first clock cycle at which the initiation flag is asserted is recorded.

6. The circuitry of claim 5, wherein a second clock cycle at which the trip flag is asserted is recorded.

7. The circuitry of claim 6, wherein a number of clock cycles between the first clock cycle and the second clock cycle is used to determine a mean value of the detected signal from the nanopore.

8. A method of measuring a detected signal from a nanopore, comprising:
   integrating by an integrating amplifier a detected signal from a nanopore;
   resetting the integrating amplifier and starting an integration of the detected signal from the nanopore based on an initiating flag; and
   terminating the integration of the detected signal from the nanopore based on a trip flag, wherein the initiation flag is re-asserted in response to the trip flag being asserted such that the detected signal from the nanopore is integrated over a plurality of integrating cycles.

9. The method of claim 8, wherein the trip flag is asserted in response to an integrated output of the integrating amplifier reaching a predetermined level.

10. The method of claim 9, wherein the trip flag is used as a feedback signal to the integrating amplifier for terminating the integration of the detected signal from the nanopore.

11. The method of claim 8, wherein a state of the trip flag is output to an external processor for processing.

12. The method of claim 8, further comprising recording a first clock cycle at which the initiation flag is asserted.

13. The method of claim 12, further comprising recording a second clock cycle at which the trip flag is asserted.

14. The method of claim 13, further comprising determining a mean value of the detected signal from the nanopore based at least in part on a number of clock cycles between the first clock cycle and the second clock cycle.

* * * * *